US006277560B1

(12) United States Patent
Andrieu et al.

(10) Patent No.: US 6,277,560 B1
(45) Date of Patent: Aug. 21, 2001

(54) MIRCROORGANISM QUANTITATION AND DETECTION METHOD AND KIT USING AN EXTERNAL STANDARD

(75) Inventors: Jean-Marie Andrieu; Wei Lu, both of Paris (FR)

(73) Assignee: Microdiag, Neuilly-sur-Seine (FR)

( * ) Notice: Subject to any disclaimer, the term of this patent is extended or adjusted under 35 U.S.C. 154(b) by 0 days.

(21) Appl. No.: 09/068,319

(22) PCT Filed: Nov. 5, 1996

(86) PCT No.: PCT/FR96/01736

§ 371 Date: May 4, 1998

§ 102(e) Date: May 4, 1998

(87) PCT Pub. No.: WO97/17465

PCT Pub. Date: May 15, 1997

(30) Foreign Application Priority Data

Nov. 6, 1995 (FR) .................................................. 95 13093

(51) Int. Cl.[7] .............................. C12Q 1/68; C12Q 1/70; C12P 19/34

(52) U.S. Cl. .................................... 435/5; 435/6; 435/91.2

(58) Field of Search ................................... 435/5, 6, 91.2, 435/810

(56) References Cited

U.S. PATENT DOCUMENTS

| 5,389,512 | * | 2/1995 | Sninsky et al. | 435/5 |
| 5,552,269 | | 9/1996 | Andrieu et al. | 435/5 |
| 5,705,365 | * | 1/1998 | Ryder et al. | 435/91.1 |
| 5,710,029 | * | 1/1998 | Ryder et al. | 435/91.1 |

FOREIGN PATENT DOCUMENTS 69102817   3/1991  (WO) .

OTHER PUBLICATIONS

Arnold et al., GATA 9(4), 113–116 (1992).*
Lu and Andrieu, 1993, "Early Detection of Human Immunodeficiency Virus–Infected Asymptomatic Subjects Susceptible to Zidovudine by Quantitative Viral Coculture and Reverse–Transcription–Linked Polymerase Chain Reaction", J. Infectious Dis. 167:1014–1020.
Eron et al., 1992, "Susceptibility Testing by Polymerase Chain Reaction DNA Quantitation: A Method to Measure Drug Resistance of Human Immunodeficiency Virus Type 1 Isolates" Proc. Natl. Acad. Sci. U.S.A. 89:3241–3245.
Lu and Andrieu, 1992, "Similar Replication Capacities of Primary Human Immunodeficiency Virus Type 1 Isolates Derived from a Wide Range of Clinical Sources", J. Virol. 66:334–340.
Bourinbaiar, 1991, "HIV and gag", Nature 349:111.
Genesca et al., 1990, "Clinical Correlation and Genetic Polymorphism of the Human Immunodeficiency Virus Proviral DNA Obtained after Polymerase Chain Reaction", J. Infectious Dis. 162:1025–1030.
Kawasaki, 1989, "Amplification of RNA Sequences via Complementary DNA (cDNA)", in *Amplifications–A Forum for PCR Users*, pp. 4–6.

* cited by examiner

Primary Examiner—Kenneth R. Horlick (57) ABSTRACT

A method wherein predetermined amounts of a microorganism of interest or the DNA or RNA thereof are used as the external standard; a fraction of the genome of said microorganism is extracted, revealed using a specific method or subjected to reverse transcription and/or amplification; and the DNA or RNA concentrations of the standard and target microorganisms or the target microorganism amplification products are compared with those of the external standard to determine values for the DNA or RNA concentration or the total microorganism concentration in each target microorganism sample. The method is useful for the quantitation and detection of all microorganisms.

10 Claims, 6 Drawing Sheets

MIRCROORGANISM QUANTITATION AND DETECTION METHOD AND KIT USING AN EXTERNAL STANDARD

The present invention relates to the quantitation and detection of microorganisms. In particular, it relates to the quantitative determination and/or detection of microorganisms having a DNA or RNA genome.

The invention applies to all known microorganisms such as viruses, bacteria, bacilli, protozoa, hematozoa which have a DNA or RNA genome and affect humans, animals or plants, as well as to microorganisms such as those existing in humans, animals and plants in a pathological or normal state; and it also applies to the quantitation and detection of these same microorganisms in products originating from animals—including humans—and plants, as well as of those capable of existing in water.

Further on, the method of the invention will be described for the quantitation of infection with RNA-containing human immuno-deficiency virus (HIV) and infection with the human DNA-containing hepatitis B virus (HBV).

BACKGROUND OF THE INVENTION

At present, the study of the epidemiology, treatment and prophylaxis of human, animal and plant diseases is a priority objective of human and veterinary medicine and of agronomy or the plant hygiene industry. Identification and quantification of microorganisms in media such as tissues, biological fluids and in-vitro preparations are steps that are indispensable for the proper conduct of such projects. Taking into account the size of most microorganisms, particularly viruses, and their concentration in biological media (generally of the order of $10^1$ to $10^{12}$ microorganisms per mL), the only current technological tools that permit both molecular identification and quantitative evaluation are those which make use of genome fragment amplification. The method of genomic amplification most frequently used at the present time is called polymerase chain reaction or PCR. Thus, it is possible, by means of an enzyme, polymerase, to amplify a DNA-containing genome fragment. Likewise, it is possible to carry out a reverse transcription of RNA into DNA, and an amplification with the aid of the reverse transcriptase+polymerase couple or by an enzyme performing these two operations. Once amplified, this genome fragment or "amplificate" is specifically identified by various methods (radioactive or colored probe, fragment size).

Methods of quantitation of HIV by PCR are described, e.g., by M. Holodniy et al., *J. Infect. Dis.* 163, 862–866 (1991); S. Aoki-Sei et al., *J. AIDS Res. Hum. Retrovirus* 8, 1263–1270 (1992); P. Bagnarelli et al., *J. Virol.* 66, 7328–7335 (1992); M. Piatak Jr. et al., *Science* 259, 1749–1755 (1993); S. M. Bruisten et al., *AIDS* 7 (Suppl. 2), S15–S20 (1993).

Methods of quantitation of hepatitis C virus RNA have been described, e.g., by U. Kumar et al., *J. Virol. Methods* 47(1–2), 95–102 (1994); A. Mazin et al., *J. Clin. Microbiol.* 32(8), 1939–44 (1994); A. Ravaggi et al., *J. Clin Microbiol.* 33(2), 265–9 (1995); K. K. Young et al., *J. Clin Microbiol.* 33(3), 654–7 (1995).

Methods of quantitation of hepatitis B virus DNA have been described, e.g., by P. Lehtovaara et al., *PCR Methods Appl.* 3(3), 169–75 (1993); J. Wu et al., *J. Virol. Methods* 49(3), 331–41 (1994); H. L. Zaaijer et al., *J. Clin Microbiol.* 32(9), 2088–91 (1994); S. Kaneko et al., J. Clin. Microbiol. 27(9), 1930–33 (1989).

However, the relationship between amplified product and initial DNA or RNA is not really constant from one experiment to another; hence, the necessity of being concerned with the problem of measuring a standard whose concentrations, moreover, are known.

Until now, the PCR amplification capacities could be evaluated by means of cells wherein the genome to be determined is present in a constant number of copies only, or by means of plasmids each having a single gene fragment. In this way, it could be established that, thanks to PCR, even a single gene fragment can be specifically identified by PCR. It has also been established that a proportionality ratio exists between DNA concentrations of a plasmid that are subjected to amplification and the DNA concentrations measured after amplification. However, this proportionality ratio has been found to change from one experiment to another, because PCR amplification is a biological process, resulting from the action of polymerase, which is not controlled in such complete fashion as to make it purely physical technique.

This has led researchers and engineers of biotechnological companies to introduce standardization into every viral quantitation experiment. Until now, the standard has consisted in a series of concentrations (generally three to five) of a standard plasmid whose DNA fragment to be amplified has the same primers, and, depending on the technologies, is either of a partly different sequence or of identical sequence. The amplification ratio of the DNA of equal concentrations of two plasmids of identical primers but of different lengths and thus of different sequences (1) may be different from one case to another and (2) is not necessarily identical to that of the DNA originating from the identical native virus concentrations within the same experiment.

The problem is even more complex if it is sought to quantitate or identify RNA viruses, such as, e.g., that of AIDS (HIV). For RNA viruses, the PCR amplification step must, in effect, be combined with a reverse transcription step (abbreviated RT) which is frequently carried out either with the aid of another enzyme, reverse transcriptase, or with an enzyme possessing both actions (reverse transcription and DNA amplification). In both cases, the enzymes currently available on the market make it possible to obtain reverse transcription ratios that can vary from one experiment to another from 10:1 (that is to say, 10 copies of RNA give one copy of DNA) to 100:1 (100 copies of RNA give 1 copy of DNA). Until now, the resulting problem, namely the noncomparability of results obtained in successive experiments, has been solved by simultaneous incubation of a concentration range of a standard RNA fragment (standard transcript) using the same primers, but whose amplified part is either identical if it is used as an external standard, or different in sequence or length if it is used in co-amplification, the transcript then being incubated in the same tube as the RNA of the target microorganism to be determined. Unfortunately, it seems that the concentrations of two transcripts can be different, and be different even from those originating from RNA obtained from the identical virus concentrations.

In conclusion:

The known reverse transcription and/or amplification techniques do not furnish identical results from one experiment to another for the same sample;

It is imperative to use a standard, which may be either internal or external;

An external standard composed either of a plasmid for a DNA microorganism or a transcript RNA for an RNA microorganism permits only a relative quantitation, because the amplification ratio is not necessarily identical to that of the DNA or RNA of the complete microorganism;

Moreover, a co-amplified internal standard involves different lengths or sequences of the plasmid or the transcript, and has the same drawbacks as an external standard using a plasmid or a transcript.

In the present state of the art, amplification of the DNA of a plasmid is not truly proportional to that undergone by viral DNA. As for the standard currently used for RNA viruses, it is a transcript which has the same drawbacks as a plasmid, to which is added the possibility of free RNA degradation.

Hence, there has been a need for microorganism quantitation and detection tests yielding absolute values of the number of target microorganisms.

SUMMARY OF THE INVENTION

It has now been found that it is possible to quantitate or detect in an absolute fashion any DNA or RNA microorganism, provided that:

(1) one knows or is otherwise able to determine a standard concentration of the microorganism or the concentration of the DNA or RNA contained in this microorganism, called standard microorganism; and (2) one compares the quantity of the product of reverse transcription and/or amplification of the RNA or DNA originating from an unknown concentration of the microorganism with amplificate quantities originating from the RNA or DNA of several known concentrations of said microorganism.

Such a process constitutes the first object of the present invention.

According to an alternative embodiment, step (2) may essentially consist of a comparative revealing based on the comparison of concentrations of the standard with concentrations of the target microorganism as detected preferably by means of the so-called branched DNA method or any other revealing method which does not amplify the DNAs or the RNAs of the standard or of the target microorganism.

To prepare known microorganism concentrations, one proceeds in accordance with any of the techniques known to those skilled in the art, preferably by centrifuging and purifying (from human, animal or plant samples of the medium to be tested, or from cell cultures) any quantity of the microorganism to be determined, then extracting the DNA or RNA from these purified centrifuged preparations by conventional means. The quantities to be used in the next phase of the process are chosen at will, the only requirement being that they be sufficient to ultimately obtain quantities of DNA or RNA of the standard microorganism that are measurable by direct microbiological methods which do not use PCR-type amplification and are within the capacity of a person skilled in the art. In actual practice, and keeping in mind the precision of equipment currently available in laboratories for these measurements, quantities of the order of several hundred manograms or a few micrograms are appropriate.

The process of the invention advantageously comprises the following steps:

1) A certain quantity of the microorganism to be determined is taken from human, animal or plant samples or from cell cultures, and then purified, the quantity of microorganism being advantageously sufficient to ensure that the target DNA or RNA concentrations are measurable by direct methods;

2) The DNA or RNA is extracted and the quantity collected (expressed in ng or µg) is measured;

3) In other respects, the number of nucleotide bases of the microorganism in question is made use of, this number being known, e.g., from databanks, or be determinable by conventional methods;

4) The total molecular mass of the DNA or RNA of said microorganism is calculated from this number of nucleotide bases, keeping in mind the mean molecular mass of one nucleotide, which is also known (about 330 daltons);

5) Using Avogadro's number ($6.02 \times 10^{23}$), the quantity of DNA or RNA of each microorganism is calculated in this manner;

6) A range of standard microorganism concentrations obtained by successive dilutions of the microorganism previously standardized according to its DNA or RNA concentrations is prepared and/or used, to form an external standard for which (a) the DNA or RNA concentration and (b) the microorganism concentration is thus known for each dilution;

7) The DNA or RNA of the standard and target microorganisms is extracted, and the extracts are subjected concurrently to a revealing by means of the so-called branched DNA method or any other revealing method which does not amplify the DNAs or the RNAs of the standard or of the target microorganism and/or to reverse transcription and/or to at least one amplification and the resulting values are recorded; and 8) The concentrations of DNAs or RNAs of both the standard and the target microorganisms are compared or the amplification products of the target microorganisms are compared with those of the external standard, to deduce the DNA or RNA or total microorganism concentration values in each target microorganism sample.

The following may be cited as examples of bibliographic sources containing indications or databank references relating to the number of nucloetide bases of microorganisms: *Virus Res.* 23, 39–53 (1992); *Gene* 81, 275–284 (1989); *Virology* 177, 305–311 (1990); and *J. Gen. Virol.* 69, 2575–2583 (1988).

According to an advantageous variant which may be used if the microorganisms are sufficiently large to be detected and counted directly, notably by optical and/or electronic methods, the above steps 2) to 5) of the invention are replaced by a simple direct measurement of the number of microorganisms.

According to a most preferred embodiment, the process according to this invention may optionally comprise the addition of an internal control, preferably under the form of a heterologous plasmid DNA or transcript RNA, and the sequence and primers of which are not related to the target DNAs or RNAs. Said internal control is advantageously added to each of the samples to be examined and serves as an internal control (hereinafter "IC"), namely for controlling the amplification or RT-linked amplification efficiency.

As a variant, the preparation of known microorganism concentrations may be replaced in the process of the invention by the preparation of known concentrations of the same inactivated microorganism whose DNA or RNA remains capable of detection or quantitation by means of a revealing method such as the so-called branched DNA revealing method and/or reverse transcription and/or amplification in a manner identical to the DNA or RNA of native virus;

of a complete nucleotide sequence, extracted from the same microorganism; or of a complete nucleotide sequence produced by synthesis.

According to a particularly advantageous variant of the process of the invention, separations of known standardized concentrations of the complete DNA or RNA microorganism of the type to be quantitated or detected, or preparations of DNA or RNA concentrations of the genome of said microorganism corresponding to known concentrations of this microorganism, are prepared and stored until they are made available to the user.

For simplifying the disclosure, reference is made hereinbelow, as a mere illustrative example, to a detection accomplished by an amplification, more precisely by way of a PCR or RT-PCR. Whereas other amplification methods can be used too, such as for example the NASBA (i.e. nucleic acid sequence based assay) method.

Molecular quantitation and detection according to the invention are of great interest for both small microorganisms and larger microorganisms, but in cases where they are present in a low concentration or whose conventional empirical evaluation techniques are no longer routinely controlled in developed countries.

The invention also relates to a kit or set of means for the quantitation and detection of DNA or RNA microorganisms, essentially comprising the following, arranged in appropriate containers and/or present in the form of appropriate devices:

- A series of known standardized concentrations of the complete DNA or RNA microorganism to be quantitated or detected, or of DNA or RNA concentrations corresponding to known concentrations of said microorganism;
- Means of extraction, revealing and/or reverse transcription and/or amplification, notably by a PCR, RT-PCR or NASBA amplification of the DNA or RNA of the target and standard microorganism;
- Means for analysis of the DNA or RNA of the target and standard microorganism or of the revealing or amplification products.

The said kit or set of means may also optionally comprise an internal control, e.g. under the form of approximately $10^3$ copies/$\mu$l of a heterologous plasmid DNA or transcript RNA, as a control for the amplification or RT-linked amplification efficiency.

It should be noted that the means of analysis of the PCR or RT-PCR products may consist in means external to the kit and designed to be used in combination therewith. These means may comprise, e.g., devices and/or products for determination by electrophoresis, colorimetry, radiometry or by any other suitable analytical method.

The above process and means provide, in an original manner, an absolute quantitation of the DNA or RNA microorganisms, because the target microorganism or its genome to be determined is identical to the standard microorganism or its genome treated concurrently. Moreover, this process and these means have been found to provide a universal quantitation and identification technique, because they permit the quantitation of all microorganisms.

Besides the quantitation concerns, the process and means of the invention may be used for the detection of the minimum quantity of microorganism measurable with the current methods of reverse transcription and/or amplification of RNA or DNA microorganisms. In practice, the minimum measurable quantity is of the order of from one to five microorganisms for the DNA microorganisms, and of the order of 10 to 100 microorganisms for the RNA microorganisms.

Below, the invention is described in a more concrete manner by reference to the attached drawings which in no way limit said invention.

DETAILED DESCRIPTION OF THE PREFERRED EMBODIMENTS

Thus, by way of indication, the HIV RNA originating from a culture was concentrated, purified and extracted so as to obtain 300 ng; knowing that the total number of nucloetides of HIV is 19000 and that the molecular mass of one nucleotide is 330 daltons, it was deduced that the total molecular mass of an HIV RNA is 6,300,000 daltons. By calculation using Avogardo's number the exact number of viral genomes and hence of virus which give rise to 300 ng of RNA was obtained: approximately $3 \times 10^{10}$ viruses. Knowing the virus concentration of an aliquot portion of the purified viral preparation, a standard range of this virus can then be prepared and used in the process of the present invention.

The process of the invention assures a reliable identification and/or absolute quantitation, because the target microorganism (to be determined) is identical to the standard microorganism. Moreover the method used by this process is universal, since it permits quantitation of all microorganisms whose quantity is concurrently measurable.

This process and the kit for its implementation may be used not only for the quantitation of microorganisms in all media or specimens, but also for the detection of the minimum quantity of microorganism measurable by current methods of reverse transcription and/or amplification of RNA or DNA microorganisms.

For DNA microorganisms, the minimum measurable quantity is of the order of from 1 to 5 microorganisms, whereas it is about 10 to 100 microorganisms for RNA microorganisms.

The present invention makes a decisive contribution to advancing the means and methods of in-vitro quantitative determination of microorganisms by providing a simple and efficient means and technique for standardization of the determinations.

The invention is described in greater detail in the following examples which in no way limit the invention and in which the proportions and percentages are given in weight/weight, unless otherwise indicated.

EXAMPLE 1
Demonstration of the Interest of a Universal Standard for the Detection and Quantification of Target DNA by PCR The variation of detection sensitivity and PCR amplification efficiency for DNA originating from different concentrations of the same HBV was studied. The plasmas were obtained from chronic hepatitis B virus carriers by plasmapheresis with high HBsAg titers. HBV virion DNA was purified by centrifugation (overnight at 25,000 rpm and at 4° C. in a Spinco 25 centrifuge) through a bed of 30% (w/v) sucrose in a TEBM medium (Tris-HCl 0.01 M, pH 7.6, Na-EDTA 0.001 M, 1% bovine serum albumin, and 0.3% 2-mercapto-ethanol). The purity of the fractionated HBV virions was monitored by electron microscopy. The DNA associated with the virions was extracted by means of a commercial DNA purification kit. The virial DNA obtained was quantitated by spectro-photometry. The number of copies of viral DNA was calculated by means of the molecular mass of the virial genome of the HBV DNA. As a variant, the number of virions can also be quantitated by electron microscopy. Serial dilutions (10, 100, 1000, 10,000 copies) of the HBV DNA were subjected to a succession of identical PCR cycles (94° C. for 60 sec, 56° C. for 60 sec and 72° C. for 90 sec) with 100 pmol of HBV primer pairs specific for the C gene: (GCTTTGGGGCATGGACATTGCC (SEQ ID NO:1)/GACTACTAGATCCCTGGATGCTGG (SEQ ID NO:2)). The specific PCR products were analyzed by dot-blot hybridization with a probe terminally labeled with $\gamma$-$^{32}$P (TCAGCTCTGTATCGAGAAGCC (SEQ ID NO:3)), and the counts per minute (cpm) of each PCR signal were recorded by means of a beta radiation counter.

Figure 1:
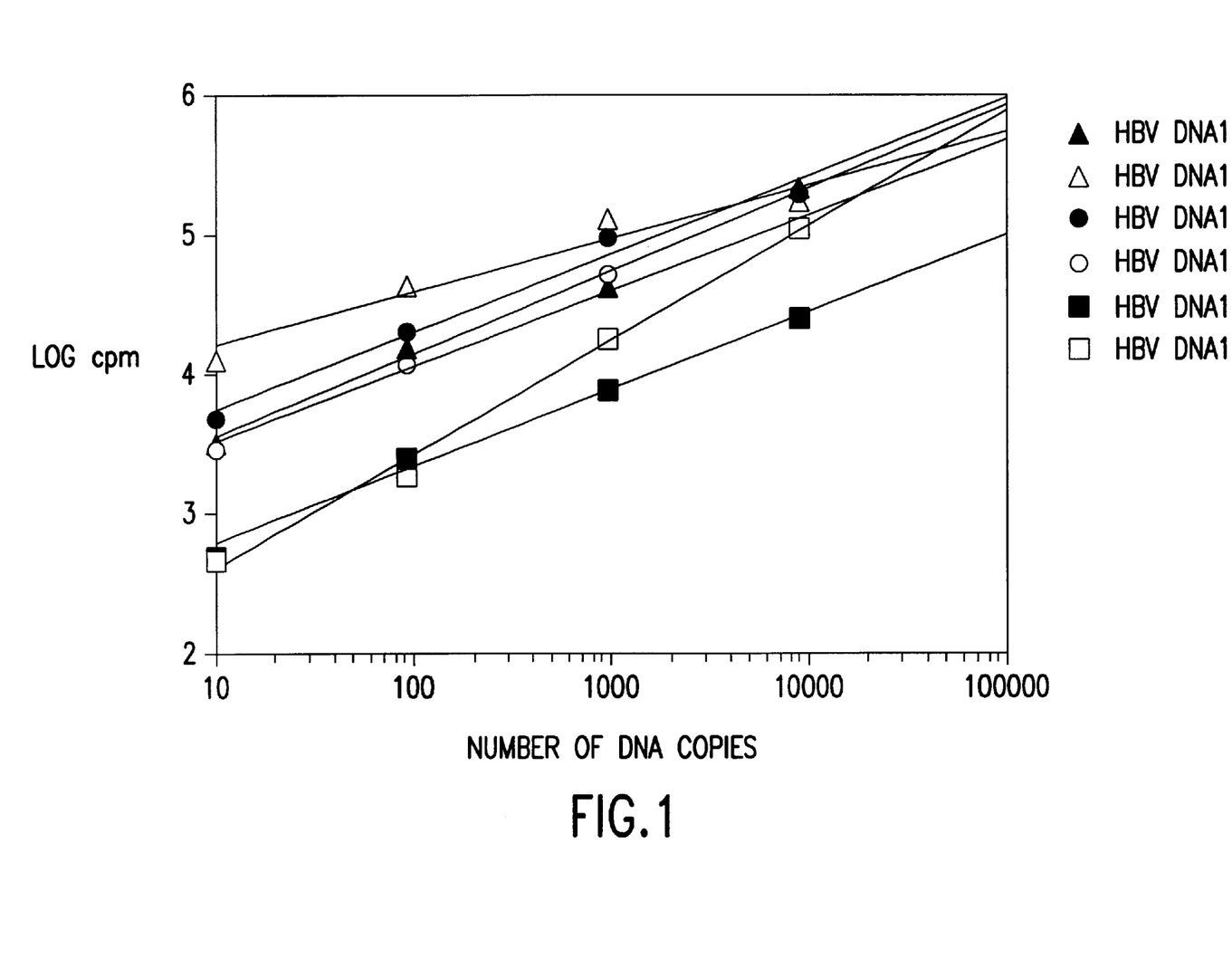
FIG. 1 is a graphic representation of the variation of detection sensitivity and amplification efficiency of different PCR experiments carried out with several different standard DNA concentrations of the same virus.

The results were recorded and plotted in graphic form in FIG. 1. It is clearly evident that the standard would give different results and should therefore be used in each experiment concurrently with the target sample.

Thus, according to the curves of FIG. 1, there exists for each DNA input of constant template (number of copies) a broad PCR product concentration interval from one experiment to another.

EXAMPLE 2
Demonstration of the Interest of a Universal Standard for the Detection and Quantification of Target RNA by RT-PCR The variation of detection sensitivity and reverse transcription/PCR amplification efficiency for RNA originating from different concentrations of the same HIV-1 were investigated. HIV-1 virion RNA was purified by passage, through a Sepharose column, of the supernatant of blood mononuclear cell blast culture infected with a primary isolate. The purity of the fractionated HIV-1 virions was monitored by electron microscopy. The RNA associated with the virions was extracted by means of a commercial RNA isolation kit. The viral RNA obtained was quantitated by spectrophotometry. The number of copies of viral RNA was calculated by means of the molecular mass of the viral genome of the HIV-1 RNA. After addition of 1 microgram of tRNA, serial dilutions (1,000,000, 100,000, 10,000, 1000 copies) of the RNA sample were pelleted and resuspended in 10 $\mu$L. A 10 $\mu$L aliquot of RNA and 1 $\mu$g of reference tRNA (free of HIV) were immediately added to each RT-PCR reaction mixture (90 $\mu$L) containing 10 units of Moloney recombinant murine leukemia virus reverse transcriptase and 3 units of DNA polymerase ampliTaq for amplification of the gag gene of HIV. The TR-PCR was carried out for 25 minutes at 42° C., for 5 minutes at 94° C., and then over 40 PCR cycles (94° C. for 60 sec, 56° C. for 60 sec, and 72° C. for 90 sec) using 100 pmol of each of the HIV primer pairs specific to the gag gene (GGAACATCAAGCAGCCATGC/TCCTTTGGTCCTTGTCTTATGTC (SEQ ID NO:5)). The specific PCR products were analyzed by dot-dot hybridization with a primer terminally labeled with $\gamma$-$^{35}$P (ATCCTGGGATTAAATAAAATAGTAAGAATGTATAGC-CCTAC) and the counts per minute (cpm) of each PCR signal were recorded with the aid of a beta radiation counter.

Figure 2:
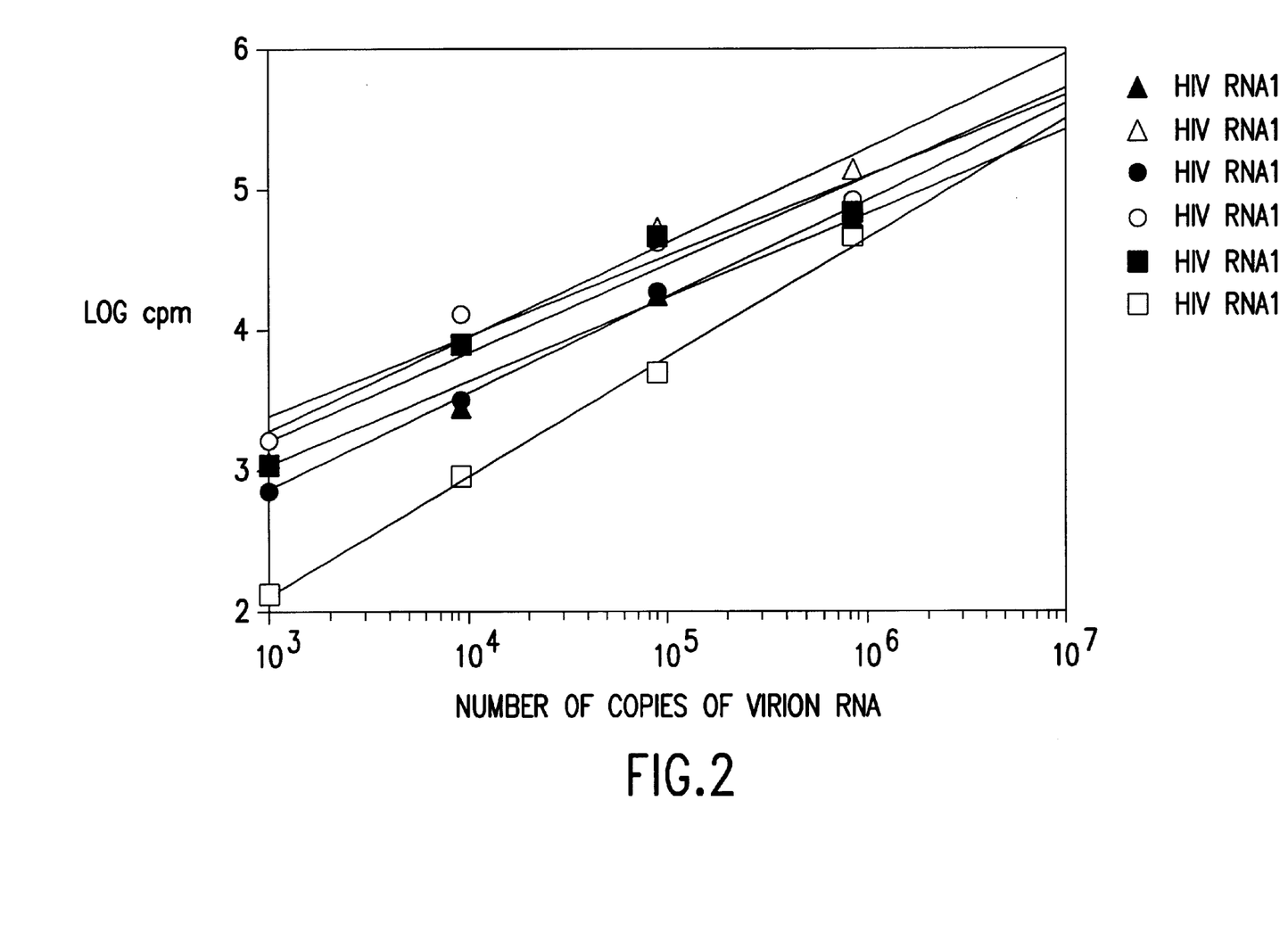
FIG. 2 is a graphic representation of the variation of detection sensitivity and amplification efficiency of different RT-PCR experiments carried out with several RNA concentrations of the same virus.

The results were recorded and plotted in graphic form in FIG. 2. It appears that the variability of the results is very great from one experient to another. Here again, it is evident that the standard would give different results and should therefore be used in each experiment concurrently with the target sample.

Thus, according to the curves of FIG. 2, there exists for each constant RNA input (number of copies) a broad PCR product concentration interval from one experiment to another.

EXAMPLE 3
Validation of a Virion DNA Standard

This example shows that the amplification efficiency is identical when using identical PCR cycles of native HBV virion DNA originating from sera of different patients infected with HBV. Serial dilutions of samples of different HBV virion DNAs prepared as in Example 1 were subjected to the same number of PCR cycles in the same experiment. The PCR product (output) was quantitated by dot blot and cpm counting.

Figure 3:
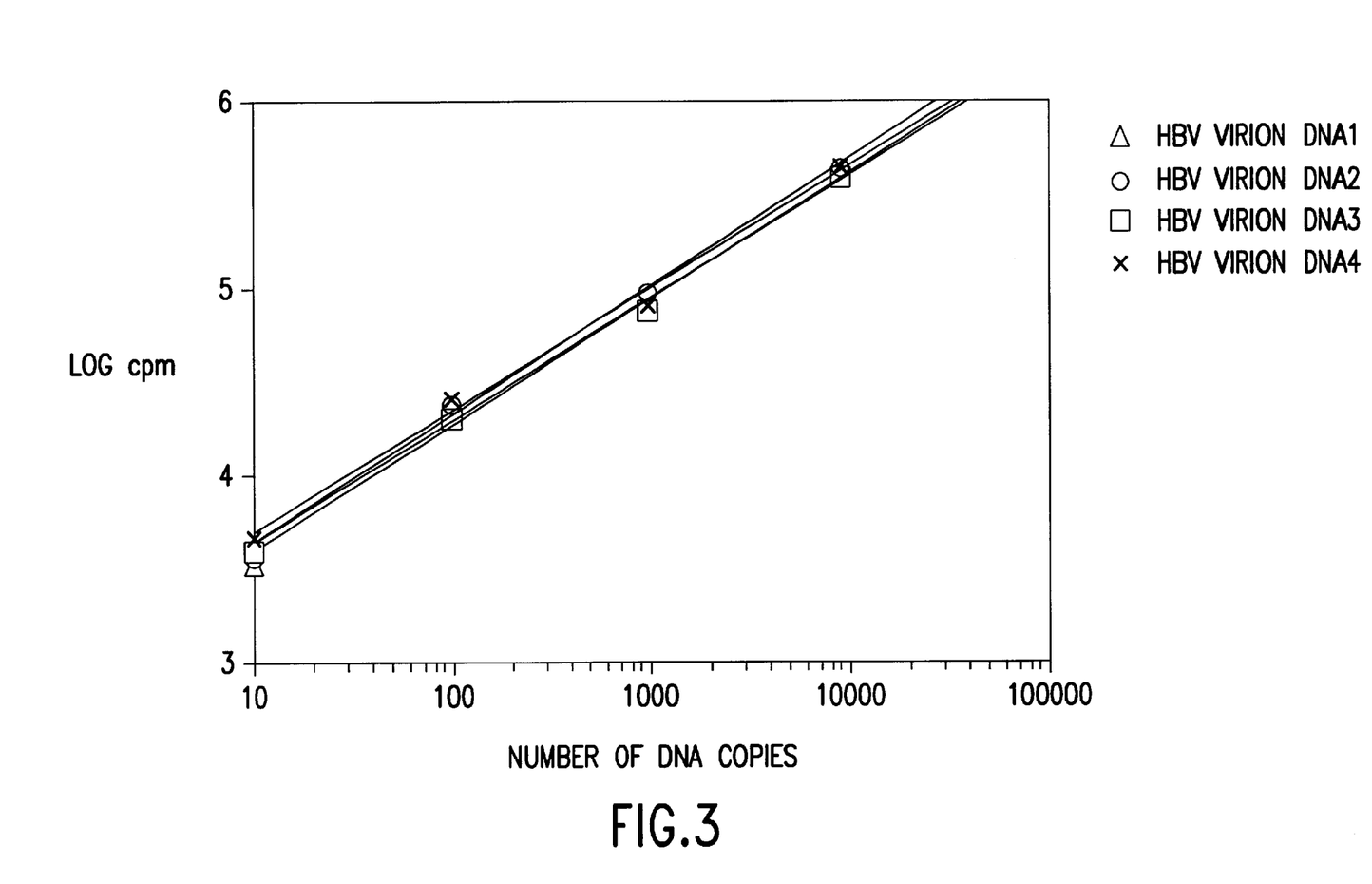
FIG. 3 is a graphic representation of the variation of amplification efficiency in PCR experiments carried out with several concentrations of DNA from virus preparations originating from different patients, within the same experiment.

The results plotted in graphic form in FIG. 3 show that the PCR amplification efficiency is identical regardless of the source of the HIV virion (in this case for 4 different sources).

EXAMPLE 4
Validation of a Virion DNA Standard

Figure 4:
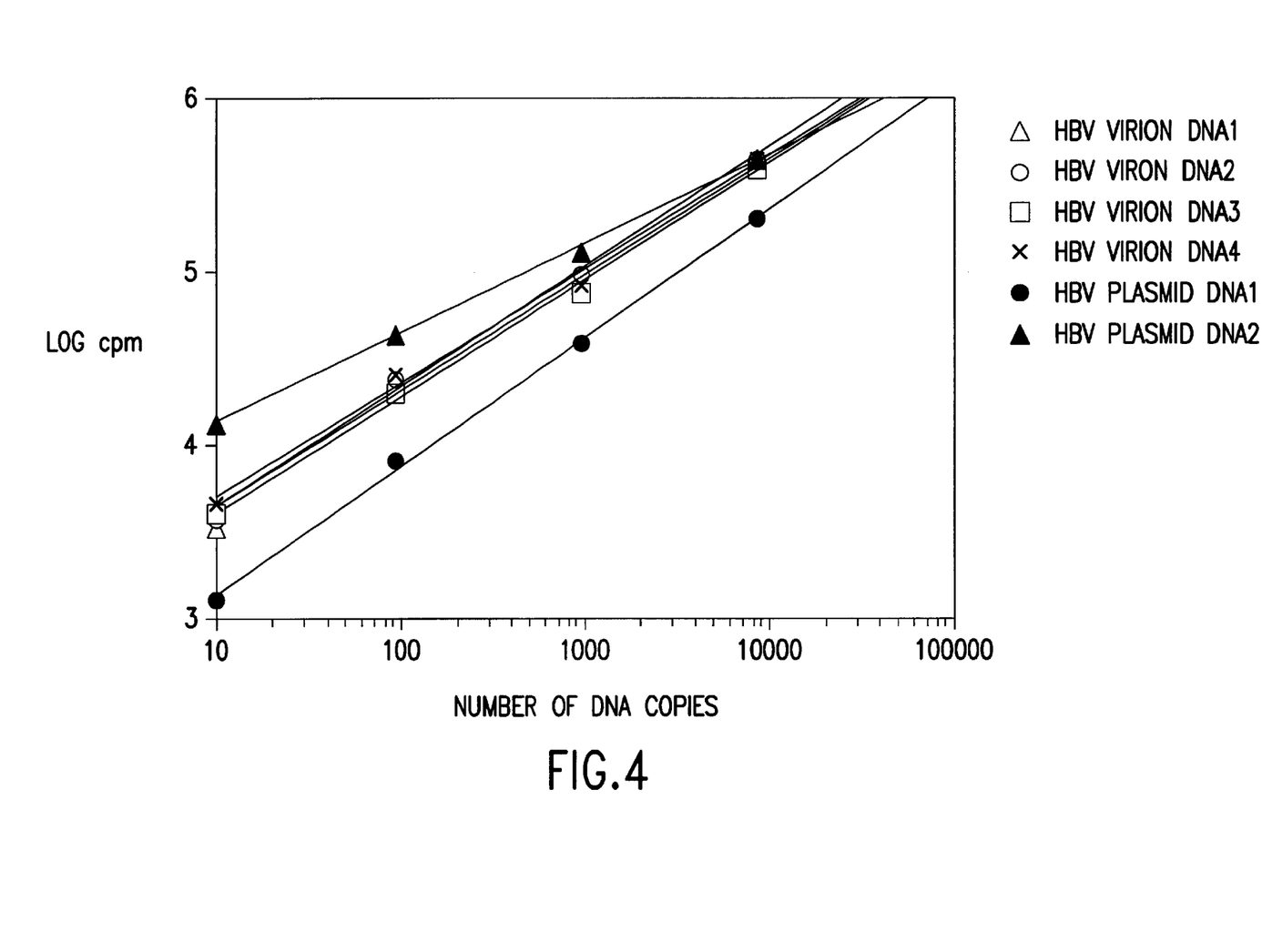
FIG. 4 is a graphic representation of the variation of amplification efficiency in PCR experiments carried out with several concentrations of DNA originating from several preparations of the same virus and with several concentrations of DNA originating from two different plasmids, respectively.

Proceeding as indicated in Example 3 but each time using, in the same PCR cycles, a native virion DNA and DNAs originating from two HBV plasmids (input), the comparative PCR amplification efficiencies could be determined (see FIG. 4).

DNA fragments of the HBV C gene sequence were produces by PCR from HBVsAg+ sera and ligated in plasmids pGEM-3Z (Promega) and pCT® (Invitrogen) (HBV plasmids DNA1 and DNA2, respectively). All constructs were confirmed by DNA sequencing with the aid of an appropriate commercial kit.

The results plotted in graphic form in FIG. 4 show that a known number of copies may or may not have an amplification efficiency comparable to that of an identical number of copies of native viral DNA originating from several samples.

It thus follows from Examples 3 and 4 that known concentrations of HBV virion DNA from different sources constitute an ideal universal standard, whereas viral DNA fragments integrated into different plasmids behave differently with respect to one another and differently from native DNAs.

EXAMPLE 5
Validation of a Virion RNA Standard

This example shows that the amplification efficiency is identical when using identical RT-PCR cycles of native HIV virion RNA originating from sera of different patients infected with HIV. Serial dilutions of samples of different HIV virion RNAs prepared as indicated in Example 2 were subjected to an RT-PCR cycle in the same experiment. The PCR product (output) was quantitated by dot blot and cpm counting.

Figure 5:
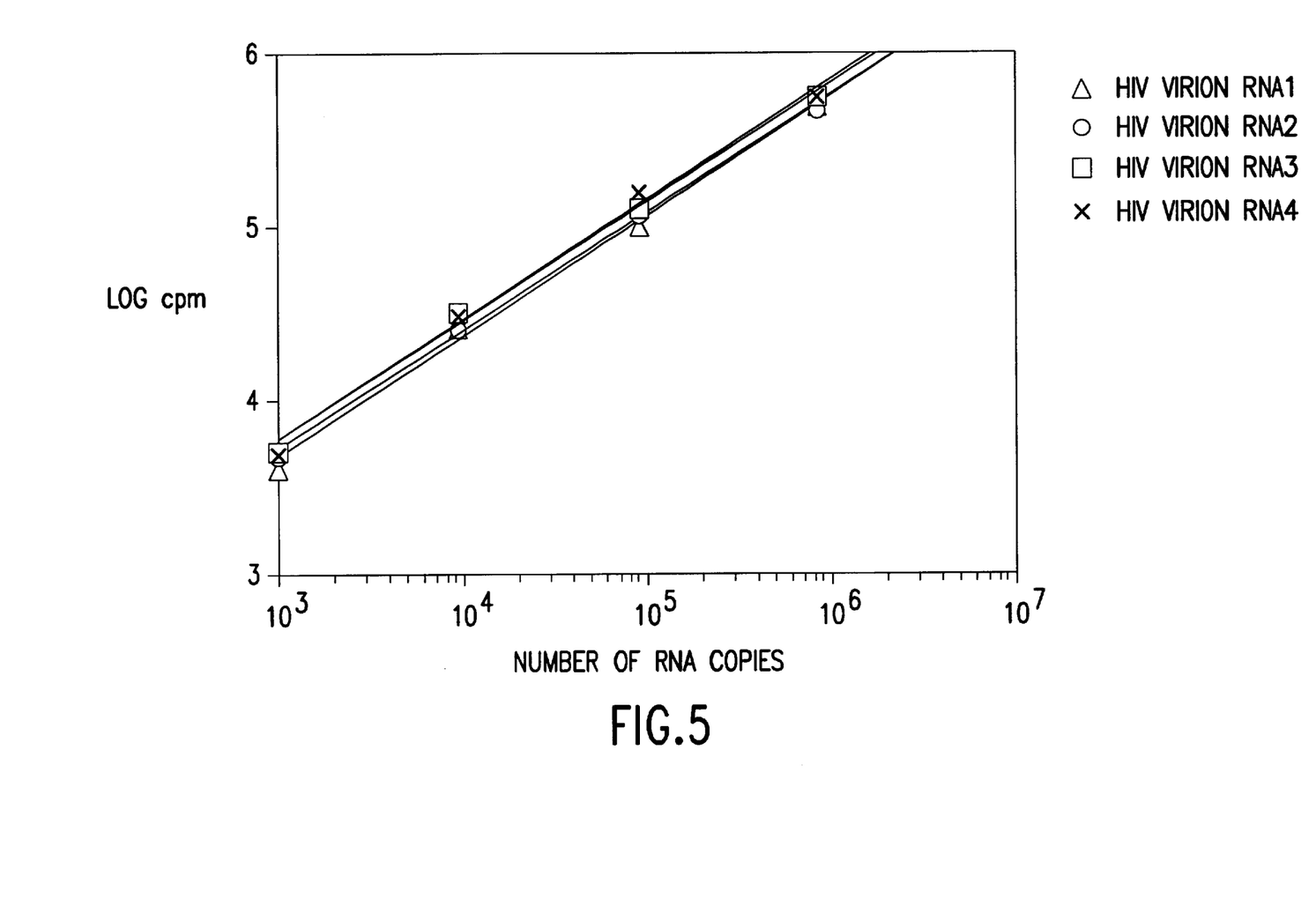
FIG. 5 is a graphic representation of the variation of amplification efficiency in RT-PCR experiments carried out with different concentrations of RNA from virus preparations originating from different patients.

The results plotted in graphic form in FIG. 5 show that the RT-PCR amplification efficiency is identical regardless of the source of the HIV virion.

EXAMPLE 6

Validation of a Virion RNA Standard

Figure 6:
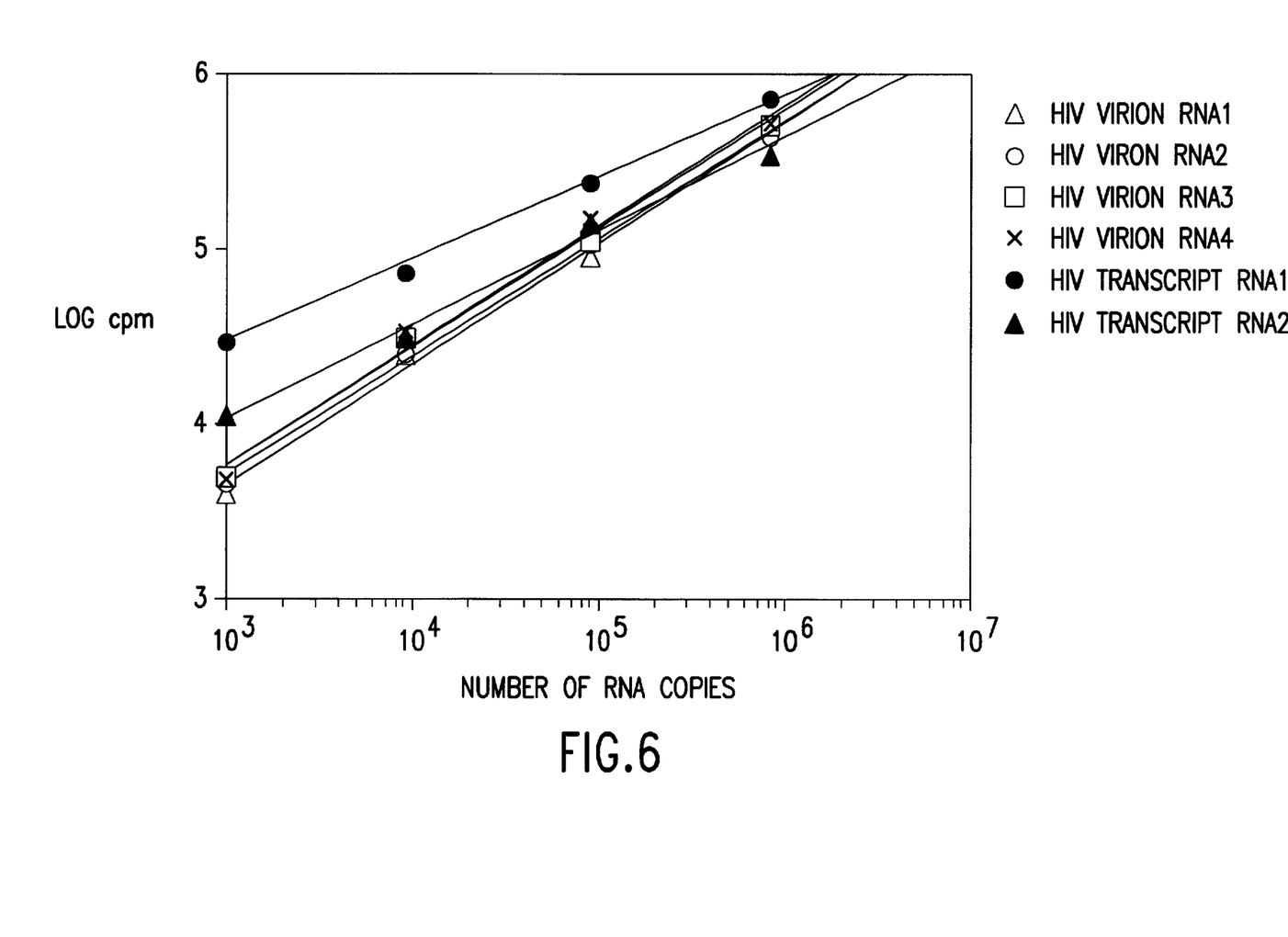
FIG. 6 is a graphic representation of the variation of amplification efficiency in RT-PCR experiments carried out with several concentrations of RNA from virus preparations originating from different patients and with two different transcript RNAs, respectively.

Proceeding as indicated in Example 5, but each time using, in the same RT-PCR cycles, a native virion RNA and a transcript RNA having a known number of copies (input), the comparative RT-PCR amplification efficiencies could be determined (see FIG. 6).

RNA fragments of HIV-1 gag sequence were produced by transcription of VIH-1 DNA templates (plasmid HIV-Z6 DNA pBR322 and plasmid $HIV_{IIIB}$ DNA pBH10-R3, respectively) with T7 RNA polymerase (HIV RNA1 and RNA2 transcripts, respectively).

The results plotted in graphic form in FIG. 6 show that the RT-PCR amplification efficiency of a transcript RNA having a known number of copies is different from that of a sample RNA.

It thus follows from Examples 5 and 6 that known concentrations HIV virion RNA of different origins constitute an ideal universal standard, whereas viral RNA fragments integrated into different plasmids behave differently with respect to one another and differently from the native RNAs.

Thus:

For monitoring the amplification efficiency in a quantitative PCR test, the use, according to the invention, of virion DNA as external standard is by far more precise and convenient than that of a plasmid DNA serving as external or internal standard.

For monitoring the amplification efficiency in a quantitative RT-PCR amplification test, the use, according to the invention, of virion RNA as external standard is by far more precise and convenient than that of a transcript RNA serving as external or internal standard.

EXAMPLE 7

Human Immunodeficiency Virus (HIV) Genome Quantitation Kit for Detection by Visualization 7.1. Introduction A human immunodeficiency virus (HIV) Genome Quantitation Kit according to this invention was designed for the detection and quantitation of HIV genomic RNA (including all HIV-0, HIV-1, and HIV-2 genotypes) in any cell-free biologic fluids (such as plasma, serum, semen, bronchoalveolar lavage fluid, etc), as well as culture supernatants. Included were reagents to perform the isolation of viral RNA using a rapid method—the reverse transcription of HIV virion RNA to cDNA using cloned Moloney murine leukemia virus reverse transcriptase—the amplification using Taq DNA polymerase—and finally the quantitative detection by a simple agarose-gel visualization procedure, which allowed a detection limit of 1000 viral RNA copies and a quantitation range of more than 4 orders of magnitude in a single test within 8 hours. Sufficient reagents were provided for 100 reactions (40 µl each) in a final 50 µl volume protocol.

The kit contained a panel of HIV Virion Standard (hereinafter "VirionStandard") as explained above ($10^4$, $10^3$, $10^2$ and 10 copies/µl provided for 4 test batches), which allowed accurate measurement of plasma/serum HIV virion RNA concentration. The kit also contained a plasmid HIV DNA ($10^2$ copies per reaction provided for 4 test batches) which served as a positive amplification signal control, as well as optionally a heterologous transcript RNA, added to each of the samples to be examined and serving as an internal control (hereinafter "IC") ($10^3$ copies per reaction provided for 100 reactions).

7.2. List of Kit Components

The HIV Genome Quantitation Kit should preferably be stored at −20° C. in a constant temperature freezer or at 4° C. with the use of an appropriate enzyme storage solution. If stored under proper conditions, the product will remain stable up to a control date printed on a label.

| No. | Reagent | Volume | Quantity | Comments |
|---|---|---|---|---|
| 1 | HIV VirionStandard | | | |
| 1a | VirionStandard 1 ($10^4$ copies/µl) | 0,4 ml | 1 | Calibrates sample RNA |
| 1b | VirionStandard 2 ($10^3$ copies/µl) | 0,4 ml | 1 | Calibrates sample RNA |
| 1c | VirionStandard 3 ($10^2$ copies/µl) | 0,4 ml | 1 | Calibrates sample RNA |
| 1d | VirionStandard 4 (10 copies/µl) | 0,4 ml | 1 | Calibrates sample RNA |
| 1e | VirionStandard 5 (HIV -negative serum) | 0,4 ml | 1 | Specificity (negative) control |
| 2 | tRNA (0,1 mg/ml) | 1 ml | 1 | Serves as carrier RNA for sample RNA |
| 3 | RNA Stocking Buffer | 250 µl | 4 | Dissolve RNA samples |
| 4 | HIV Amplification Mixture, with HIV primers and IC primers, if any | 1 ml | 4 | Hybridizes to HIV RNA and cDNA genomes |
| 5 | Enzyme Mixture | 28 µl | 4 | Reverse transcribes target RNA and amplifies cDNA |
| 6 | Plasmid HIV DNA ($10^2$ DNA copies/µl) | 40 µl | 1 | HIV cDNA (positive) signal control |
| 7 | optional IC ($10^3$ copies/µl) | 1 ml | 1 | Internal control for RT-linked amplification efficiency |
| 8 | Autoclaved Water | 40 µl | 1 | Background (negative) signal control |

7.3. Reagents and Equipments 7.3.1. Reagents

Chloroform (ACS grade)

Isopropanol (ACS grade)

75% ethanol (ACS grade)

Agarose (DNase-free)

Ethidium bromide

RNA isolation solution 7.3.2. Equipments

A microtube centrifuge (4° C.)

A vacuum facility

A lid-heating Thermal Cycler

A generator and a bath for electrophoresis 7.4. Protocol for HIV Quantitation by Reverse Transcription-Linked Genome Amplification 7.4.1. RNA Extraction 100 µl of HIV VirionStandard and plasma or serum samples were homogenized with 400 µl RNA isolation solution, with a few strokes in a homogenizer. 60 µl of chloroform were added and shaken vigorously for 15 seconds and let to stay on ice for 10 minutes. The suspension was centrifuged at 12,000 g at 4° C. for 15 minutes.

After addition of chloroform and centrifugation, the homogenate formed two phases: the lower phenol-chloroform phase (~240 µl) and the upper aqueous phase (~320 µl). The RNAs remained exclusively in the aqueous phase, whereas the DNAs and proteins were in the interphase and the organic phase.

The aqueous phase (300 µl) was transferred into fresh tubes. An equal volume of isopropanol was added and the samples were stored at −20° C. for 1 hour. The samples were centrifuged for 10 minutes at 12,000 g (4° C.) and the pellet was briefly dried. The supernatant was removed, the RNA pellet was washed once with 75% ethanol (500 µl) by vortexing, and finally the RNA pellet was dried by vacuum. The RNA pellet was dissolved in 11 µl RNA stocking buffer. RNA precipitate formed a white-yellow pellet (seen only in large quantity) at the bottom of the tube. It is important not to let the RNA pellet be completely dried, since drying greatly decreases its solubility.

7.4.2. RNA Reverse Transcription and cDNA Amplification

10 µl RNA samples and positive/negative controls were added in fresh (200 µl) tubes. 40 µl HIV reverse-transcription/amplification mixture (RTAM) (38.9 µl of HIV Amplification Mixture+1.1 µl of Enzyme Mixture) were dispensed into each tube. The tubes were transferred to a lid-heating Thermal Cycler.

42° C. for 25 minutes

94° C. for 5 minutes 35 cycles (94° C. for 35 s, 55° C. for 45 s, and 72° C. for 60 s);

Followed by 55° C. for 5 minutes and then 72° C. for 5 minutes.

7.5. Visualization and Quantitation

10 µl of the post-reaction mixture were dispensed onto 1.5% agarose gel containing 0.5 µg/ml ethidium bromide and an electrophoresis was run a 150 V for 10 minutes.

Specifically amplified HIV sequences can be readily visualized by differences in size. The copy-ranges of HIV virion RNA in 100 µl of plasma/serum samples could be estimated by comparing their amplification bands to those of HIV VirionStandard (semi-quantitation).

EXAMPLE 8

Human Immunodeficiency Virus (HIV) Genome Quantitation Kit for Detection by an Optical Density Reader 8.1. Introduction A human immunodeficiency virus (HIV) Genome Quantitation Kit according to this invention was designed for the detection and quantitation of HIV genomic RNA (including all HIV-0, HIV-1, and HIV-2 genotypes) in any cell-free biologic fluids (such as plasma, serum, semen, bronchoalveolar lavage fluid, etc), as well as culture supernatants. Included were reagents to perform the isolation of viral RNA using a rapid method—the reverse transcription of HIV virion RNA to cDNA using cloned moloney murine leukemia virus reverse transcriptase—the amplification using Taq DNA polymerase—and finally the quantitative detection by DIG-linked liquid hybridization procedure, which allowed a detection limit of 100 viral RNA copies and a quantitation range of about 2 orders of magnitude in a single test within 8 hours. Sufficient reagents were provided for 100 reactions (40 µl each) in a final 50 µl volume protocol.

The kit contained a panel of HIV VirionStandard ($10^3$, $10^2$, 10, and 1 copies/µl provided for 4 test batches), which allowed accurate measurement of plasma/serum HIV virion RNA concentration. The kit also contained a plasmid HIV DNA ($10^2$ copies per reaction provided for 4 test batches) which served as a positive amplification signal control, as well as optionally a heterologous transcript RNA, added to each of the samples to be examined and serving as a IC ($10^3$ copies per reaction provided for 100 reactions).

8.2. List of Kit Components

The HIV Genome Quantitation Kit should preferably be stored at −20° C. in a constant temperature freezer or at 4° C. with the use of an appropriate enzyme storage solution. If stored under proper conditions, the product will remain stable up to a control date printed on a label.

| No. | Reagent | Volume | Quantity | Comments |
|---|---|---|---|---|
| I Reverse Transcription (RT)-Linked HIV Genome Amplification and DIG Labelling | | | | |
| 1 | HIV VirionStandard | | | |
| 1a | VirionStandard 1 ($10^3$ copies/µl) | 0,4 ml | 1 | Calibrates sample RNA |
| 1b | VirionStandard 2 ($10^2$ copies/µl) | 0,4 ml | 1 | Calibrates sample RNA |
| 1c | VirionStandard 3 (10 copies/µl) | 0,4 ml | 1 | Calibrates sample RNA |
| 1d | VirionStandard 4 (1 copie/µl) | 0,4 ml | 1 | Calibrates sample RNA |
| 1e | VirionStandard 5 (HIV negative serum) | 0,4 ml | 1 | Specificity (negative) control |
| 2 | tRNA (0,1 mg/ml) | 1 ml | | Serves as carrier RNA for sample RNA |
| 3 | RNA Stocking Buffer | 250 µl | 4 | Dissolve RNA samples |
| 4 | HIV Amplification and IC primers (5% of DIG-dUTP) | 1 ml | 4 | Hybridizes to HIV RNA and cDNA genomes |
| 5 | Enzyme Mixture | 28 µl | 4 | Reverse transcribes target RNA and amplifies cDNA |
| 6 | Plasmid HIV DNA ($10^2$ DNA copies/µl) | 40 µl | 1 | HIV cDNA (positive) control signal |
| 7 | Heterologous Transcript RNA ($10^3$ copies/µl) | 1 ml | 1 | Internal control for RT-linked amplification efficiency |
| 8 | Autoclaved Water | 40 µl | 1 | Background (negative) signal control |
| II Liquid Hybridization and DIG Detection | | | | |
| 9 | Biotinylated HIV Probe | 200 µl | 1 | Capture of HIV cDNA in liquid hybridization |
| 10 | Biotinylated Internal Control DNA-specific Probe | 100 µl | 1 | Capture of IC cDNA in liquid hybridization |
| 11 | Denaturation Buffer | 4 ml | 1 | Allows denaturation of amplified dsDNA |
| 12 | Hybridization Buffer | 40 ml | 1 | Allows hybridization of probe to target DNA |

-continued

| No. | Reagent | Volume | Quantity | Comments |
|---|---|---|---|---|
| 13 | Washing Buffer (10x) | 50 ml | 1 | Removes non-specific DNA |
| 14 | Streptavidin-Coated Bead (or Microplate) | 200 (8 wells) | 1 (24) | Capture of hybridized HIV cDNA in liquid hybridization |
| 15 | Anti-DIG-POD Working Solution | 40 ml | 1 | Binds to DIG molecules of specifically amplified product |
| 16 | ABTS Substrate Solution | 40 ml | 1 | Allows color development in POD system |

8.3. Reagents and Equipments 8.3.1. Reagents

Chloroform (ACS grade)

Isopropanol (ACS grade)

75% ethanol (ACS grade)

RNA isolation solution

Streptavidin-coated microplate 8.3.2. Equipments

A microtube centrifuge (4° C.)

A vacuum facility

A lid-heated Thermal Cycler

A water bath or incubator for liquid hybridization

An automated optical density reader 8.4. Protocol for HIV Quantitation by Reverse Transcription-Linked Genome Amplification 8.4.1. RNA Extraction 100 µl of HIV VirionStandard and plasma or serum samples were homogenized with 400 µl RNA isolation solution, with a few strokes in a homogenizer. 60 µl of chloroform were added and shaken vigorously for 15 seconds and let to stay on ice for 10 minutes. The suspension was centrifuged at 12,000 g at 4° C. for 15 minutes.

After addition of chloroform and centrifugation, the homogenate formed two phases: the lower phenol-chloroform phase (~240 µl) and the upper aqueous phase (~320 µl). The RNAs remained exclusively in the aqueous phase, whereas the DNAs and proteins were in the interphase and the organic phase.

The aqueous phase (300 µl) was transferrred into fresh tubes. An equal volume of isopropanol was added and the samples were stored at –20° C. for 1 hour. The samples were centrifuged for 10 minutes at 12,000 g (4° C.) and the pellet was briefly dried. The supernatant was removed, the RNA pellet was washed once with 75% ethanol (500 µl) by vortexing, and finally the RNA pellet was dried by vacuum. The RNA pellet was dissolved in 11 µl RNA stocking buffer.

RNA precipitate formed a white-yellow pellet (seen only in large quantity) at the bottom of tube. It is important not to let the RNA pellet be completely dried, since drying greatly decreases its solubility.

8.4.2. RNA Reverse Transcription and cDNA Amplification

10 µl RNA samples and positive/negative controls were added in fresh (200 µl) tubes. 40 µl HIV reverse-transcription/amplification mixture (RTAM) (38.7 µl of HIV Amplification Mixture+1.1 µl of Enzyme Mixture+0.2 µl of DIG-dUTP) were dispensed into each tube. The tubes were transferred to a lid-heating Thermal Cycler.

42° C. for 25 minutes

94° C. for 5 minutes 36 cycles (94° C. for 35 s, 55° C. for 45 s, and 72° C. for 60 s);

Followed by 55° C. for 5 minutes and then 72° C. for 5 minutes.

8.5. Detection and Quantitation

A 2 µl amplified product (×2) and a 10-fold dilution (×2) were added into fresh tubes and mixed with 18 µl of denaturation solution at room temperature for 10 minutes. After filling up 180 µl hybridization solution (×4) containing HIV probe and IC probe, vortexing, then pipeting in a well of streptavidin-coated microplate, followed by 2 hours incubation at 37° C. on a shaker, the solution was discarded and each well was washed 3 times with 200 µl wahing buffer. 200 µl of the anti-DIG-POD working solution were added, followed by 30 minutes incubation at 37° C. on a shaker. After washing 3 times with 200 µl washing buffer, 200 µl ABTS substrate solution were added to each well, followed by 30 minutes incubation at 37° C. with shaking. The plate was kept in the dark during the incubation. The absorbance was read at 405 nm. The numbers of HIV particles per ml of each plasma/serum sample can be reported by an automatic computer system using the standard curve generated from HIV VirionStandard (absolute quantitation).

EXAMPLE 9

Human Immunodeficiency Virus (HIV) Genome Quantitation Kit for Detection by Fluorescence 9.1. Introduction A human immunodeficiency virus (HIV) Genome Quantitation Kit according to this invention was designed and performing as described in Example 8, except for the quantitation range which was of more than 4 orders of magnitude in a single test within 7 hours.

9.2. List of Kit Components

The HIV Genome Quantitation Kit should preferably be stored at –20° C. in a constant temperature freezer or at 4° C. with the use of an appropriate enzyme storage solution. If stored under proper conditions, the product will remain stable up to a control date printed on a label.

| No. | Reagent | Volume | Quantity | Comments |
|---|---|---|---|---|
| I Reverse Transcription (RT)-Linked HIV Genome Amplification | | | | |
| 1 | HIV VirionStandard | | | |
| 1a | VirionStandard 1 ($10^3$ copies/µl) | 0,4 ml | 1 | Calibrates sample RNA |
| 1b | VirionStandard 2 ($10^2$ copies/µl) | 0,4 ml | 1 | Calibrates sample RNA |
| 1c | VirionStandard 3 (10 copies/µl) | 0,4 ml | 1 | Calibrates sample RNA |
| 1d | VirionStandard 4 (1 copie/µl) | 0,4 ml | 1 | Calibrates sample RNA |
| 1e | VirionStandard 5 (HIV negative serum) | 0,4 ml | 1 | Specificity (negative) control |
| 2 | tRNA (0,1 mg/ml) | 1 ml | 1 | Serves as carrier RNA for sample RNA |
| 3 | RNA Stocking Buffer | 250 µL | 4 | Dissolve RNA samples |
| 4 | HIV Amplification Mixture, with HIV primers and IC primers | 1 ml | 4 | Hybridizes to HIV RNA and cDNA genomes |

-continued

| No. | Reagent | Volume | Quantity | Comments |
|---|---|---|---|---|
| 5 | Enzyme Mixture | 28 µl | 4 | Reverse transcribes target RNA and amplifies cDNA |
| 6 | Plasmid HIV DNA ($10^2$ DNA copies/µl) | 40 µl | 1 | HIV cDNA (positive) signal control |
| 7 | Heterologous Transcript RNA ($10^3$ copies/µl) | 1 ml | 1 | Internal control for RT-linked amplification efficiency |
| 8 | Autoclaved Water | 40 µl | 1 | Background (negative) signal control |
| II Liquid Hybridization and Fluorescence Counting | | | | |
| 9 | HIV Probes (+ & − strains)-Coated Microplate | 8 wells | 12 | Capture of HIV cDNA in liquid hybridization |
| 10 | IC-Probe-Coated Microplate | 8 wells | 12 | Capture of IC cDNA in liquid hybridization |
| 11 | Denaturation Buffer | 2 ml | 1 | Allows denaturation of amplified dsDNA |
| 12 | Hybridization Buffer | 20 ml | 1 | Allows hybridization of probe to target DNA |
| 13 | Washing Buffer | 100 ml | 1 | Retains specifically amplified DNA in the microplate |
| 14 | Fluorochrome | 10 ml | 1 | Allows post-amplification dsDNA detection |

9.3. Reagents and Equipments
 9.3.1. Reagents
 Chloroform (ACS grade)
 Isopropanol (ACS grade)
 75% ethanol (ACS grade)
 RNA isolation solution
 9.3.2. Equipments
 A microtube centrifuge (4° C.)
 A vacuum facility or a centrifuge pump
 A lid-heating Thermal Cycler
 A water bath or incubator for liquid hybridization
 A sensitive fluorometer
9.4. Protocol for HIV Quantitation by Reverse Transcription-Linked Genome Amplification
 9.4.1. RNA Extraction
 100 µl of HIV VirionStandard and plasma or serum samples were homogenized with 400 µl RNA isolation solution, with a few strokes in a homogenizer. 60 µl of chloroform were added and shaken vigorously for 15 seconds and let to stay on ice for 10 minutes. The suspension was centrifuged at 12,000 g at 4° C. for 15 minutes.

After addition of chloroform and centrifugation, the homogenate formed two phases: the lower phenol-chloroform phase (~240 µl) and the upper aqueous phase (~320 µl). The RNAs remained exclusively in the aqueous phase, whereas the DNAs and proteins were in the interphase and the organic phase.

The aqueous phase (300 µl) was transferred into fresh tubes. An equal volume of isopropanol was added and the samples were stored at −20° C. for 1 hour. The samples were centrifuged for 10 minutes at 12,000 g (4° C.) and the pellet was briefly dried. The supernatant was removed, the RNA pellet was washed once with 75% ethanol (500 µl) by vortexing, and finally the RNA pellet was dried by vacuum. The RNA pellet was dissolved in 11 µl RNA stocking buffer.

RNA precipitate formed a white-yellow pellet (seen only in large quantity) at the bottom of tube. It is important not to let the RNA pellet be completely dried, since drying greatly decreases its solubility.

9.4.2. RNA Reverse Transcription and cDNA Amplification

10 µl RNA samples and positive/negative controls were added in fresh (200 µl) tubes. 40 µl HIV reverse-transcription/amplification mixture (RTAM) (38.9 µl of HIV Amplification Mixture+1.1 µl of Enzyme Mixture) were dispensed into each tube. The tubes were transferred to a lid-heating Thermal Cycler.

42° C. for 25 minutes
 94° C. for 5 minutes
 35 cycles (94° C. for 35 s, 55° C. for 45 s, and 72° C. for 60 s);
 Followed by 55° C. for 5 minutes and then 72° C. for 5 minutes.

9.5. Detection and Quantitation
 5 µl (×2) of the post-reaction mixture were added into fresh tubes and mixed with 15 µl of denaturation solution at room temperature for 10 minutes. After filling up 180 µl (×2) hybridization solution, vortexing, then pipeting in a well of HIV-probes-coated microplate, followed by 2 hours incubation at 37° C. with shaking, the solution was discarded and each well was washed 3 times with 200 µl wahing buffer. 100 µl of fluorochrome solution were added, followed by the transfer of the microplate to an automated fluorometer for fluorescence counting and report printing.

EXAMPLE 10

Human Immunodeficiency Virus (HIV) Genome Quantitation Kit for Detection by Chemoluminescence 10.1. Introduction A human immunodeficiency virus (HIV) Genome Quantitation Kit according to this invention was designed and performing as described in Example 8, except for the quantitation range which was of more than 4 orders of magnitude in a single test within 7 hours.

10.2. List of Kit Components

The HIV Genome Quantitation Kit should preferably be stored at −20° C. in a constant temperature freezer. If stored under proper conditions, the product will remain stable up to a control date printed on a label.

| No. | Reagent | Volume | Quantity | Comments |
|---|---|---|---|---|
| I Reverse Transcription (RT)-Linked HIV Genome Amplification | | | | |
| 1 | HIV VirionStandard | | | |
| 1a | VirionStandard 1 ($10^3$ copies/µl) | 0,4 ml | 1 | Calibrates sample RNA |
| 1b | VirionStandard 2 ($10^2$ copies/µl) | 0,4 ml | 1 | Calibrates sample RNA |
| 1c | VirionStandard 3 (10 copies/µl) | 0,4 ml | 1 | Calibrates sample RNA |
| 1d | VirionStandard 4 (1 copie/µl) | 0,4 ml | 1 | Calibrates sample RNA |

-continued

| No. | Reagent | Volume | Quantity | Comments |
|---|---|---|---|---|
| 1e | VirionStandard 5 (HIV negative serum) | 0,4 ml | 1 | Specificity (negative) control |
| 2 | tRNA (0,1 mg/ml) | 1 ml | 1 | Serves as carrier RNA for sample RNA |
| 3 | RNA Stocking Buffer | 250 μl | 4 | Dissolve RNA samples |
| 4 | HIV Amplification Mixture, with biotinylated HIV and IC primers | 1 ml | 4 | Hybridizes to HIV RNA and cDNA genomes |
| 5 | Enzyme Mixture | 28 μl | 4 | Reverse transcribes target RNA and amplifies cDNA |
| 6 | Plasmid HIV DNA ($10^2$ DNA copies/μl) | 40 μl | 1 | HIV cDNA (positive) signal control |
| 7 | Heterologous Transcript RNA ($10^3$ copies/μl) | 1 ml | 1 | Internal control for RT-linked amplification efficiency |
| 8 | Autoclaved Water | 40 μl | 1 | Background (negative) signal control |
| II Liquid Hybridization and Chemoluminescence Labelling | | | | |
| 9 | HIV-Specific Probe | 100 μl | 1 | Hybridizes specifically to HIV cDNA |
| 10 | IC DNA-Specific Probe | 100 μl | 1 | Hybridizes specifically to the IC cDNA |
| 11 | Denaturation Buffer | 5 ml | 1 | Allows denaturation of amplified dsDNA |
| 12 | Hybridization Buffer | 50 ml | 1 | Allows hybridization of probe to target DNA |
| 13 | Washing Buffer (10x) | 50 ml | 1 | Removes non-specific DNA in the microplate |
| 14 | Streptavidin-Coated Bead (or Microplate) | 200 (8 wells) | 1 (24) | Capture of hybridized HIV cDNA in liquid hybridization |
| 15 | Anti-dsDNA-APL Working Solution | 10 ml | 1 | Labelling of hybridized target DNA |
| 16 | Chemo-luminescent Substrate Solution | 10 ml | 1 | Allows luminescence detection and quantitation |

10.3. Reagents and Equipments

10.3.1. Reagents

Chloroform (ACS grade)
Isopropanol (ACS grade)
75% ethanol (ACS grade)
RNA isolation solution

10.3.2. Equipments

A microtube centrifuge (4° C.)
A vacuum facility or a centrifuge pump
A lid-heating Thermal Cycler
A water bath or incubator for liquid hybridization
A luminometer

10.4. Protocol for HIV Quantitation by Reverse Transcription-Linked Genome Amplification

10.4.1. RNA Extraction

100 μl of HIV VirionStandard and plasma or serum samples were homogenized with 400 μl RNA isolation solution, with a few strokes in a homogenizer. 60 μl of chloroform were added and shaken vigorously for 15 seconds and let to stay on ice for 10 minutes. The suspension was centrifuged at 12,000 g at 4° C. for 15 minutes.

After addition of chloroform and centrifugation, the homogenate formed two phases: the lower phenol-chloroform phase (~240 μl) and the upper aqueous phase (~320 μl). The RNAs remained exclusively in the aqueous phase, whereas the DNAs and proteins were in the interphase and the organic phase.

The aqueous phase (300 μl) was transferred into fresh tubes. An equal volume of isopropanol was added and the samples were stored at −20° C. for 1 hour. The samples were centrifuged for 10 minutes at 12,000 g (4° C.) and the pellet was briefly dried. The supernatant was removed, the RNA pellet was washed once with 75% ethanol (500 μl) by vortexing, and finally the RNA pellet was dried by vacuum. The RNA pellet was dissolved in 11 μl RNA stocking buffer.

RNA precipitate formed a white-yellow pellet (seen only in large quantity) at the bottom of tube. It is important not to let the RNA pellet be completely dried, since drying greatly decreases its solubility.

10.4.2. RNA Reverse Transcription and cDNA Amplification

10 μl RNA samples and positive/negative controls were added in fresh (200 μl) tubes. 40 μl HIV reverse-transcription/amplification mixture (RTAM) (38.9 μl of HIV Amplification Mixture+1.1 μl of Enzyme Mixture) were dispensed into each tube. The tubes were transferred to a lid-heating Thermal Cycler.

42° C. for 25 minutes
94° C. for 5 minutes
35 cycles (94° C. for 35 s, 55° C. for 45 s, and 72° C. for 60 s)
Followed by 55° C. for 5 minutes and then 72° C. for 5 minutes.

10.5. Detection and Quantitation

5 μl (×2) of the post-reaction mixture were added into 2 fresh tubes and mixed with 15 μl of denaturation solution at room temperature for 10 minutes. After filling up 180 μl (×2) hybridization solution containing HIV-specific probe or the internal control (IC)-DNA-specific probe, vortexing, then pipeting in the tube of streptavidin-coated bead or in the well of streptavidin-coated microplate, followed by 2 hours incubation at 37° C. with shaking, the solution was discarded and each well was washed 3 times with 200 μl wahing buffer. 200 μl of the anti-dsDNA antibodies conjugated with alkaline phosphatase (APL) were added, followed by incubation for 30 minutes at 37° C. on a shaker. After washing 3 times with 200 μl washing buffer, 100 μl of chemoluminescent substrate solution were added. Then, the microplate was immediately transferred to a luminometer for chemoluminescence counting and report printing. The numbers of HIV particles per ml of each plasma/serum sample can be reported by an automatic computer system using the standard curve generated from HIV VirionStandard (absolute quantitation)

EXAMPLE 11

Human Hepatitis B Virus (HBV) Genome Quantitation Kit for Detection by Chemoluminescence

11 1. Introduction

A human hepatitis B virus (HBV) Genome Quantitation Kit according to this invention was designed for the detection and quantitation of HBV genomic DNA in any cell-free biologic fluids (such as plasma, serum, semen, bronchoalveolar lavage fluid, etc). Included were reagents to perform the isolation of viral DNA using a rapid method, the amplification of HBV virion DNA using Taq DNA polymerase, and quantitative detection by a chemoluminescence-linked liquid hybridization procedure, which allowed a detection limit of 50 viral DNA copies and a quantitation range of over 4 orders of magnitude in a single test within 5 hours. Sufficient reagents were provided for 100 reactions (40 µl each) in a final 50 µl volume protocol.

The kit contained a panel of HBV VirionStandard ($10^4$, $10^3$, $10^2$ and 10 copies/µl provided for 4 test batches), which allowed accurate measurement of plasma/serum HBV virion DNA concentration. The kit also contained a plasmid HBV DNA ($10^3$ copies per reaction provided for 4 test batches) which served as a positive amplification signal control, as well as optionally a heterologous plasmid DNA, added to each of the samples to be examined and serving as a IC ($10^3$ copies per reaction provided for 100 reactions).

11.2. List of Kit Components

The HBV Genome Quantitation Kit should preferably be stored at −20° C. in a constant temperature freezer or at 4° C. with the use of an appropriate enzyme storage solution. If stored under proper conditions, the product will remain stable up to a control date printed on a label.

| No. | Reagent | Volume | Quantity | Comments |
|---|---|---|---|---|
| | I HBV Genome Amplification | | | |
| 1 | HBV VirionStandard | | | |
| 1a | VirionStandard 1 ($10^4$ copies/µl) | 0,2 ml | 1 | Calibrates sample DNA |
| 1b | VirionStandard 2 ($10^3$ copies/µl) | 0,2 ml | 1 | Calibrates sample DNA |
| 1c | VirionStandard 3 ($10^2$ copies/µl) | 0,2 ml | 1 | Calibrates sample DNA |
| 1d | VirionStandard 4 (10 copies/µl) | 0,2 ml | 1 | Calibrates sample DNA |
| 1e | VirionStandard 5 (HBV negative serum) | 0,2 ml | 1 | Specificity (negative) control |
| 2 | HBV Amplification Mixture, with biotinylated HBV and IC primers | 1,1 ml | 4 | Hybridizes to HBV DNA genome |
| 3 | Taq DNA Polymerase | 25 µl | 1 | Amplifies target DNA |
| 4 | Plasmid HBV DNA ($10^2$ DNA copies/µl) | 50 µl | 1 | HBV cDNA (positive) signal control |
| 5 | Heterologous Plasmid DNA ($10^2$ DNA copies/µl) | 1 ml | 1 | Internal control for amplification efficiency |
| 6 | Autoclaved Water | 100 µl | 1 | Background (negative) signal control |
| 7 | DNA Discharge Buffer | | | |
| | II Liquid Hybridization and Chemoluminescence Labelling | | | |
| 8 | HBV-Specific Probe | 100 µl | 1 | Hybridizes specifically to HBV cDNA |
| 9 | IC DNA-Specific Probe | 100 µl | 1 | Hybridizes specifically to the IC DNA |
| 10 | Denaturation Buffer | 5 ml | 1 | Allows denaturation of amplified dsDNA |
| 11 | Hybridization Buffer | 50 ml | 1 | Allows hybridization of probe to target DNA |
| 12 | Washing Buffer (10x) | 50 ml | 1 | Removes non-specific DNA |
| 13 | Streptavidin-Coated Bead (or Microplate) | 200 (8 wells) | 1 (24) | Capture of hybridized HBV cDNA in liquid hybridization |
| 14 | Anti-dsDNA-APL Working Solution | 10 ml | 1 | Labelling of hybridized target DNA |
| 15 | Chemoluminescent Substrate Solution | 10 ml | 1 | Allows luminescence detection and quantitation |

11.3. Equipments Required

A microtube centrifuge

A lid-heating Thermal Cycler

A water bath for liquid hybridization

A luminometer

11.4. Protocol for Sample Preparation and Amplification

11.4.1. Sample Preparation

50 µl of HBV VirionStandard and plasma or serum samples were homogeneized with 50 µl of DNA discharge buffer, and then led to stay at 98° C. for 15 minutes. The tubes were centrifuged at 7,500 g for 10 minutes.

After centrifugation, the DNAs remained exclusively in the liquid phase (10–15 µl) whereas the proteins were in the pellet.

11.4.2. cDNA Amplification

10 µl of the liquid phase were transferred to fresh (200 µl) tubes. 40 µl HBV amplification mixture (40 µl of HBV Amplification Mixture+5 µl Taq DNA polymerase) were dispensed into each tube. The tubes were transferred to a lid-heating Thermal Cycler.

94° C. for 5 minutes;

35 cycles (94° C. for 35 s, 60° C. for 45 s, and 72° C. for 60 s);

Followed by a 5 minute extension at 72° C.

11.5. Visualization and Quantitation

5 µl (×2) of the post-reaction mixture were added into 2 fresh tubes in parallel and mixed with 15 µl of denaturation solution at room temperature for 10 minutes. After filling up 180 µl (×2) hybridization solution containing HBV-specific probe or the IC-DNA-specific probe, vortexing, then pipeting in the tube of streptavidin-coated bead or in the well of streptavidin-coated microplate, followed by 2 hours incubation at 37° C. with shaking, the solution was discarded and each well was washed 3 times with 200 µl wahing buffer. 200 µl of anti-dsDNA antibodies conjugated with alkaline phosphatase (APL) were added, followed by incubation for 30 minutes at 37° C. on a shaker. After washing 3 times with 200 μl washing buffer, 100 μl of chemoluminescent substrate solution were added. Then, the microplate was immediately transferred to a luminometer for chemoluminescence counting and report printing. The numbers of HBV particles per ml of each plasma/serum sample can be reported by an automatic computer system using the standard curve generated from HIV VirionStandard (absolute quantitation)

What is claimed is:

1. A method for quantitating the amount of a target microorganism in a sample comprising the steps of:
   (1) preparing nucleic acid from the sample;
   (2) subjecting the nucleic acid prepared in step (1) to a process selected from the group consisting of reverse transcription, amplification using microorganism-specific primers, reverse transcription followed by amplification using microorganism-specific primers, and non-amplifying methods of quantitating nucleic acid, to produce a sample product;
   (3) preparing nucleic acid from a known quantity of a purified standard microorganism, such that the target microorganism and the standard microorganism are essentially identical;

(4) subjecting the nucleic acid prepared in step (3) to the same process selected in step (2) to produce a standard product; and (5) determining the amount of target microorganism by comparing the amount of sample product with the amount of standard product.

2. The method according to claim 1, wherein the process utilized in steps (2) and (4) is a branched DNA method of Quantitating DNA without amplification.

3. The method according to claim 1, where step (3) further comprises the following steps:

(a) sampling and purifying a given quantity of the microorganism from a source selected from the group consisting of a human, an animal, a plant, and cell cultures thereof, wherein the quantity of microorganism purified is sufficient to provide a measurable nucleic acid concentration without amplification;

(b) extracting nucleic acid from the microorganism purified in step (a);

(c) measuring the quantity of nucleic acid extracted in step (b);

(d) calculating the total molecular mass of the nucleic acid of the target microorganism using the number of nucleotide bases in the microorganism and the mean molecular mass of one nucleotide;

(e) calculating the quantity of nucleic acid in each microorganism using the total molecular mass measured in step (d) and Avogadro's number; and (f) preparing a series of external standard solutions containing nucleic acid concentrations representative of known numbers of microorganisms by preparing a range of dilutions of the nucleic acid extracted in step (b) and determining the number of microorganisms represented in each dilution using the number calculated in step (e).

4. The method according to claim 1, where step (3) further comprises the following steps:

(a) sampling and purifying a given quantity of the microorganism from a source selected from the group consisting of a human, an animal, a plant, and cell cultures thereof;

(b) directly measuring the number of microorganisms purified; and (c) preparing a series of external standard solutions representative of known numbers of microorganisms by preparing a range of dilutions of the microorganisms purified in step (a).

5. The method according to claim 1, wherein the process used in step (2) and (4) is selected from the group consisting of amplification using microorganism-specific primers, and reverse transcription followed by amplification using microorganism-specific primers, further comprising the following step:

(6) using an internal control which is selected from the group consisting of a heterologous plasmid DNA and an RNA transcript, where the internal control is unrelated to the nucleic acid of the target microorganism and is used to evaluate the efficiency of amplification.

6. The method according to claim 1, where, in step (3), the source of nucleic acid is selected from the group consisting of (a) an inactivated form of the microorganism, (b) nucleic acid extracted from the microorganism, and (c) a synthetic version of the nucleic acid of the microorganism.

7. The method according to claim 1, 2, 3 or 4, where standard concentrations of microorganism nucleic acids to be used as external standards are prepared and stored prior to use.

8. A kit for the quantitation and detection of a target microorganism, comprising:

(a) a series of solutions having known standardized concentrations of genomic nucleic acid of a purified standard microorganism, where the target microorganism and the standard microorganism are essentially identical; and (b) means for performing a step selected from the group consisting of extracting nucleic acid, reverse transcribing nucleic acid, amplifying nucleic acid, detecting nucleic acid and a combination thereof, wherein the nucleic acid may be present in a solution according to (a) or may be present in a test sample.

9. The kit according to claim 8, which further comprises a means for directly measuring the number of microorganisms.

10. The kit according to claim 8, further comprising an internal control which is selected from the group consisting of a heterologous plasmid DNA and an RNA transcript, where the internal control is unrelated to the nucleic acid of the target microorganism and is used to evaluate the efficiency of amplification.

* * * * *

```
                        SEQUENCE LISTING

<160> NUMBER OF SEQ ID NOS: 6

<210> SEQ ID NO 1
<211> LENGTH: 22
<212> TYPE: DNA
<213> ORGANISM: Hepatitis B Virus

<400> SEQUENCE: 1
gctttggggc atggacattg cc                                          22

<210> SEQ ID NO 2
<211> LENGTH: 24
<212> TYPE: DNA
<213> ORGANISM: Hepatitis B Virus

<400> SEQUENCE: 2
gactactaga tccctggatg ctgg                                        24

<210> SEQ ID NO 3
<211> LENGTH: 21
<212> TYPE: DNA
<213> ORGANISM: Hepatitis B Virus

<400> SEQUENCE: 3
tcagctctgt atcgagaagc c                                           21

<210> SEQ ID NO 4
<211> LENGTH: 20
<212> TYPE: DNA
<213> ORGANISM: Human Immunodeficiency Virus

<400> SEQUENCE: 4
ggaacatcaa gcagccatgc                                             20

<210> SEQ ID NO 5
<211> LENGTH: 23
<212> TYPE: DNA
<213> ORGANISM: Human Immunodeficiency Virus

<400> SEQUENCE: 5
tcctttggtc cttgtcttat gtc                                         23

<210> SEQ ID NO 6
<211> LENGTH: 41
<212> TYPE: DNA
<213> ORGANISM: Human Immunodeficiency Virus

<400> SEQUENCE: 6
atcctgggat taaataaaat agtaagaatg tatagcccta c                     41
```